United States Patent
Benneker et al.

(10) Patent No.: US 6,844,469 B2
(45) Date of Patent: Jan. 18, 2005

(54) PROCESS FOR THE PRODUCTION OF CYCLOHEXANONE OXIME

(75) Inventors: Arno Benneker, Geleen (NL); Paulus Johannes Jacobus Pieters, Stein (NL); Alex Pit, Evans, GA (US); Henk Oevering, Elsloo (NL)

(73) Assignee: DSM Ip Assets B.V., Heerlen (NL)

( * ) Notice: Subject to any disclaimer, the term of this patent is extended or adjusted under 35 U.S.C. 154(b) by 0 days.

(21) Appl. No.: 10/297,180

(22) PCT Filed: May 31, 2001

(86) PCT No.: PCT/NL01/00427

§ 371 (c)(1),
(2), (4) Date: Sep. 12, 2003

(87) PCT Pub. No.: WO01/94296

PCT Pub. Date: Dec. 13, 2001

(65) Prior Publication Data

US 2004/0039230 A1 Feb. 26, 2004

(30) Foreign Application Priority Data

Jun. 5, 2000 (EP) ............................................. 00201965
Jun. 5, 2000 (EP) ............................................. 00201970

(51) Int. Cl.$^7$ ........................ C07C 249/08; C01B 21/14
(52) U.S. Cl. ........................ 564/267; 564/253; 564/259
(58) Field of Search ................................. 564/253, 259, 564/267

(56) References Cited

U.S. PATENT DOCUMENTS

| 3,720,758 A | 3/1973 | Aggenbach et al. |
| 3,862,230 A | 1/1975 | Elmendorp et al. |
| 3,997,607 A | 12/1976 | De Rooij et al. |

FOREIGN PATENT DOCUMENTS

| GB | 1 138 750 A | 1/1969 |

*Primary Examiner*—Brian Davis
(74) *Attorney, Agent, or Firm*—Mayer, Brown, Rowe & Maw LLP

(57) ABSTRACT

The invention relates to a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone to form cyclohexanone oxime, where the concentration hydroxylammonium in the aqueous reaction medium entering the cyclohexanone oxime synthesis zone is higher than 1.0 mol/l.

10 Claims, 1 Drawing Sheet

PROCESS FOR THE PRODUCTION OF CYCLOHEXANONE OXIME

CROSS REFERENCE TO RELATED APPLICATIONS

This application is the National Phase of International Application PCT/NL01/00427 filed May 31, 2001 which designated the U.S., and which further claims priority to European application No. 00201970.1, filed Jun. 5, 2000, and European application No. 00201965.1, filed Jun. 5, 2000, all of which are hereby incorporated in their entirety by reference.

The invention relates to a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone in the presence of an organic solvent to form cyclohexanone oxime.

Such a process is known from U.S. Pat. No. 3,997,607 describing a process for the production of cyclohexanone oxime in which a buffered, aqueous reaction medium containing buffer acids or acidic salts, for example phosphate buffer, is continuously recycled between a hydroxylammonium synthesis zone, in which nitrate ions are catalytically reduced with molecular hydrogen to hydroxylammonium, and an oximation zone where cyclohexanone is converted to cyclohexanone oxime. Before the aqueous reaction medium is passed into the hydroxylammonium synthesis zone, it is enriched with the required nitrate ions by addition of nitric acid or by absorption of nitrous gases in the aqueous reaction medium in which instance nitric acid is formed in situ. After having been enriched in hydroxylammonium in the hydroxylammonium synthesis zone, the aqueous reaction medium is passed to the oxime synthesis zone, where the hydroxylammonium reacts with cyclohexanone, forming the corresponding oxime. The oxime can then be separated from the aqueous reaction medium which is recycled to the hydroxylammonium synthesis zone.

The net chemical reactions occurring during the process can be represented by the following equations:

1) Preparation of the hydroxylammonium:

$$2H_3PO_4 + NO_3^- + 3H_2 \rightarrow NH_3OH^+ + 2H_2PO_4^- + 2H_2O$$

2) Preparation of the oxime

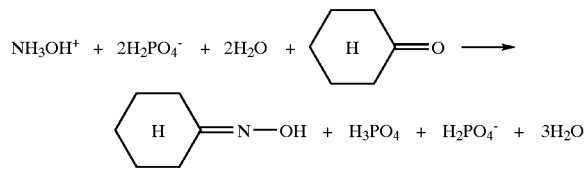

3) Supply of $HNO_3$ to make up the depletion of the source of nitrate ions after removal of the oxime formed

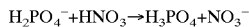

$$H_2PO_4^- + HNO_3 \rightarrow H_3PO_4 + NO_3^-$$

In the process of U.S. Pat. No. 3,997,607, the aqueous reaction medium leaving the cyclohexanone oxime synthesis zone contains unconverted hydroxylammonium. It is described that hydroxylammonium present in the aqueous reaction medium can decompose when the aqueous reaction medium is subjected to a heat treatment in the presence of nitrous gases at elevated temperatures. In the process of U.S. Pat. No. 3,997,607 the heat treatment is carried out to remove organic contaminants from the aqueous reaction medium.

In a recycle process, it is often possible to recycle unconverted reactants, in which case an incomplete conversion does not result in a loss of reactants. However, we found that, even without the heat treatment described in U.S. Pat. No. 3,997,607, decomposition of hydroxylammonium occurs in the aqueous reaction medium which is recycled from the cyclohexanone oxime synthesis zone to the hydroxylammonium synthesis zone. The decomposition is in particular found to occur following the addition of nitric acid to the aqueous reaction medium or during the formation of nitric acid by absorption of nitrous gases in the aqueous reaction medium.

We have found that the quantity of hydroxylammonium lost by decomposition per quantity of hydroxylammonium formed in the hydroxylammonium synthesis zone is decreased by increasing the concentration hydroxylammonium in the aqueous reaction medium entering the cyclohexanone oxime synthesis zone.

Therefore, the invention provides a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone in the presence of an organic solvent to form cyclohexanone oxime, characterized in that the concentration hydroxylammonium in the aqueous reaction medium entering the cyclohexanone oxime synthesis zone is higher than 1.0 mol/l.

According to the invention, only small quantities of hydroxylammonium are lost by decomposition per quantity of hydroxylammonium formed in the hydroxylammonium synthesis zone (and per quantity of cyclohexanone oxime formed in the cyclohexanone oxime synthesis zone). Moreover, a high conversion of hydroxylammonium towards cyclohexanone oxime can be achieved.

According to the invention, the concentration hydroxylammonium in the aqueous reaction medium entering the cyclohexanone oxime synthesis zone is higher than 1.0 mol/l. Preferably, the concentration hydroxylammonium in the aqueous reaction medium entering the cyclohexanone oxime synthesis zone is higher than 1.1 mol/l, more preferably higher than 1.2 mol/l, more preferably higher than 1.4 mol/l, in particular higher than 1.6 mol/l. Increasing the concentration hydroxylammonium in the aqueous reaction medium entering the cyclohexanone oxime synthesis zone has the advantage that the quantity of hydroxylammonium lost by decomposition per quantity of hydroxylammonium formed in the hydroxylammonium synthesis zone (and per quantity of cyclohexanone oxime formed in the cyclohexanone oxime synthesis zone) is decreased. Moreover, the conversion of hydroxylammonium is increased. An increased concentration hydroxylammonium in the aqueous reaction medium entering the cyclohexanone oxime synthesis zone may for instance be achieved by increasing the residence time in the hydroxylammonium synthesis zone and/or by increasing the nitrate concentration in the aqueous reaction medium entering the hydroxylammonium synthesis zone. There is no specific upper limit for the concentration hydroxylammonium in the aqueous reaction medium entering the cyclohexanone oxime synthesis zone. Generally, the concentration hydroxylammonium in the aqueous reaction medium entering the cyclohexanone oxime synthesis zone is below 2.5 mol/l.

Preferably, the concentration hydroxylammonium in the aqueous reaction medium exiting the cyclohexanone oxime synthesis zone is less than 0.1 mol/l, more preferably less than 0.08 mol/l, in particular less than 0.05 mol/l. The concentration hydroxylammonium in the aqueous reaction medium exiting the cyclohexanone oxime synthesis zone is generally higher than 0.005 mol/l, in particular higher than 0.01 mol/l. Preferably, the conversion of hydroxylammonium is higher than 90%, more preferably higher than 95%. As used herein the conversion is defined as $(c(NH_3OH^+)_{in} - c(NH_3OH^+)_{out})/c(NH_3OH^+)_{in}(\times 100\%)$ wherein $c(NH_3OH^+)_{in}$ represents the concentration hydroxylammonium in the aqueous reaction medium entering the cyclohexanone oxime synthesis zone and $c(NH_3OH^+)_{out}$ represents the concentration hydroxylammonium in the aqueous reaction medium exiting the cyclohexanone oxime synthesis zone.

In the cyclohexanone oxime synthesis zone, hydroxylammonium is reacted with cyclohexanone in the presence of an organic solvent to form cyclohexanone oxime. Typically, the organic solvent and cyclohexanone are fed to the cyclohexanone oxime synthesis zone, and an organic medium comprising the organic solvent and the cyclohexanone oxime are withdrawn from the cyclohexanone oxime synthesis zone. Preferably, the aqueous reaction medium and a stream comprising the cyclohexanone and the organic solvent are contacted in countercurrent flow. A suitable process is for instance described in GB-A-1,138,750. Use may be made of known types of counterflow reactors, such as for instance pulsed columns filled with packing bodies or rotating disc reactors. It is also possible to use a system comprising a number, e.g. 3 to 6, of series-connected reactors equipped with stirrers, each of these reactors also being provided with a liquid-liquid separator. Any organic solvent may be used in which cyclohexanone and cyclohexanone oxime may be dissolved, such as for instance alcohols, ketones, esters, ethers, hydrocarbons, and mixtures of the same. Preferably, the organic solvent has a solubility in water of less than 0.1% by weight at 20° C. Preferably, the organic solvent is selected from the group consisting of benzene, toluene, xylene, methylcyclopentane, cyclohexane and mixtures thereof. Most preferably, the organic solvent is toluene. Preferably, the cyclohexanone is dissolved in the organic solvent.

There is no specific lower limit for the concentration cyclohexanone oxime in the organic medium exiting the cyclohexanone oxime synthesis zone. Generally, the cyclohexanone oxime concentration in the organic medium exiting the cyclohexanone oxime synthesis zone is higher than 5 wt. %. Preferably, the cyclohexanone oxime concentration in the organic medium exiting the oxime synthesis zone is higher than 25 wt. %, more preferably higher than 30 wt. %, in particular higher than 35 wt. %, more in particular higher than 38 wt. %. Increasing the cyclohexanone concentration in the organic medium exiting the oxime synthesis zone is an effective way of separating increased amounts of cyclohexanone oxime from the cyclohexanone oxime synthesis zone. Generally, the cyclohexanone oxime concentration in the organic medium exiting the cyclohexanone oxime synthesis zone, is lower than 95 wt. %, preferably lower than 80 wt. %, more preferably lower than 60 wt. %. All cyclohexanone oxime concentrations in the organic medium are given relative to the sum weight of the cyclohexanone oxime plus organic solvent.

The cyclohexanone oxime synthesis zone may be operated at a temperature ranging from 40 to 150° C. and at atmospheric, sub-atmospheric, or elevated pressures, preferably between 0.05 and 0.5 MPa, more preferably between 0.1 and 0.2 MPa, most preferably between 0.1 and 0.15 MPa. Preferably, the aqueous reaction medium entering the cyclohexanone oxime synthesis zone has a pH of between 1 and 6, more preferably between 1.5 and 4.

In a preferred embodiment, the cyclohexanone oxime synthesis zone comprises a reaction zone in which hydroxylammonium is reacted with cyclohexanone to form cyclohexanone oxime by contacting the aqueous reaction medium and the stream comprising the cyclohexanone and the organic solvent in countercurrent flow, and an extraction zone in which the aqueous reaction medium and an organic solvent are contacted, preferably in countercurrent flow, the aqueous reaction medium entering the cyclohexanone oxime synthesis zone being fed to the reaction zone, the aqueous reaction medium exiting the reaction zone being fed to the extraction zone. This embodiment has the advantage that organic residuals which have an adverse effect on the activity of the catalyst, in particular cyclohexanone and cyclohexanone oxime, are separated from the aqueous reaction medium exiting the reaction zone. Preferably, cyclohexanone is fed to the oxime synthesis zone between the reaction zone and the extraction zone. Preferably, organic solvent exiting the extraction zone is fed to the reaction zone. Preferably, cyclohexanone is fed to the cyclohexanone oxime synthesis zone in the organic solvent entering the extraction zone. Use may be made of known types of extractors such as for instance an extraction column, or one or more reactors quipped with stirrers, optionally series-connected, each of these reactors also being provided with a liquid-liquid separator. Preferably, a pulsed column filled with packing bodies is used. The reaction zone and extraction zone are preferably operated at a temperature ranging from 40 to 150° C. and at atmospheric, sub-atmospheric, or elevated pressures, preferably between 0.05 and 0.5 MPa, more preferably between 0.1 and 0.2 MPa, most preferably between 0.1 and 0.15 MPa. Use may be made of known types of extractors such as for instance extraction columns, preferably, pulsed columns filled with packing bodies, or one or more reactors equipped with stirrers, optionally series-connected, each of these reactors also being provided with a liquid-liquid separator. Preferably, the organic solvent has a solubility in water of less than 0.1% by weight at 20° C. Preferably, the organic solvent is selected from the group consisting of benzene, toluene, xylene, methylcyclopentane, cyclohexane and mixtures thereof. Most preferably, the organic solvent is toluene. The operating conditions for the reaction zone and the extraction zone are not necessarily the same. Preferably, the same solvent is used in the reaction zone and the extraction zone. Preferably, the joint content of the cyclohexanone and cyclohexanone oxime in the aqueous reaction medium exiting the cyclohexanone oxime synthesis zone is below 0.2 wt. % (2000 ppm), preferably below 0.1 wt. %, more preferably below 0.05 wt. %, in particular below 0.02 wt. %, more in particular below 0.01 wt. %, most preferably below 0.005 wt. % (relative to the weight of the aqueous reaction medium).

Preferably, the aqueous reaction medium exiting the cyclohexanone oxime synthesis zone is subjected to one or more separation steps prior to entering the hydroxylammonium synthesis zone in order to reduce the amount of organic contaminants, in particular cyclohexanone and cyclohexanone oxime. Preferably, the aqueous reaction medium exiting the cyclohexanone oxime synthesis zone or exiting the extraction zone is subjected to stripping to achieve further reduction in organic contaminants. The stripping process described in U.S. Pat. No. 3,940,442 may for instance be used. It is preferred that the joint content of cyclohexanone and cyclohexanone in the aqueous reaction medium entering the hydroxylammonium synthesis zone is not more than 0.02 wt. % (200 ppm), more preferably not more than 0.005 wt. %, in particular not more than 0.002 wt. %, more in particular not more than 0.001 wt. % and most preferably not more than 0.0002 wt. % (relative to the weight of the aqueous reaction medium).

We have found that an increase of the concentration hydroxylammonium in the aqueous reaction medium entering the cyclohexanone oxime synthesis zone may result in an increase of the concentration of organic contaminants, in particular cyclohexanone and cyclohexanone oxime, in the aqueous reaction medium exiting the cyclohexanone oxime synthesis zone. These organic contaminants may for instance be separated using one or more of the separation processes described above.

We have found that an increased phosphate concentration in the aqueous reaction medium entering the cyclohexanone oxime synthesis zone results in a decrease of the concentration of the organic contaminants in the aqueous reaction medium which is recycled from the cyclohexanone oxime synthesis zone to the hydroxylammonium synthesis zone. Generally, the phosphate concentration in the aqueous reaction medium entering the cyclohexanone oxime synthesis zone is higher than 2.0 mol/l, preferably higher than 2.5 mol/l, more preferably higher than 3.0 mol/l, in particular higher than 3.3 mol/l, more in particular higher than 3.5 mol/l, most preferably higher than 3.7 mol/l. Increasing the phosphate concentration has the advantage that an effect of the increased concentration hydroxylammonium on the concentration organic contaminants in the aqueous reaction medium exiting the cyclohexanone oxime synthesis zone is mitigated or avoided. Preferably, the phosphate concentration is chosen such that no crystallization occurs, which depends, inter alia, on the temperature and the concentration of other components in the aqueous reaction medium. Generally, the phosphate concentration in the aqueous reaction medium entering the cyclohexanone oxime synthesis zone is lower than 8 mol/l, preferably lower than 5 mol/l, more preferably lower than 4.5 mol/l. As used herein, the phosphate concentration denotes the sum concentration of all phosphates, irrespective of the form in which they are present, expressed in mol per liter of aqueous reaction reaction medium. Preferably, the phosphates are present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof. Preferably, in the aqueous reaction medium entering the cyclohexanone oxime synthesis zone, the ratio c(phosphate)/c($NH_3OH^+$) is higher than 2.0, more preferably higher than 2.1, in particular higher than 2.2, more in particular higher than 2.3, wherein c(phosphate) represents the phosphate concentration (in mol/l) and c($NH_3OH^+$) represents the concentration hydroxylammonium (in mol/l). An increased ratio is advantageous, since it results in a decrease of the amount of organic contaminants entering the hydroxylammonium synthesis zone under further equal circumstances. There is no specific upper limit for the ratio. If the ratio is too high, the process may become less attractive from an economical point of view. In general, the ratio c(phosphate)/c($NH_3OH^+$) is less than 10.

We have found that a decreased molar ratio of (hydroxylammonium fed to the cyclohexanone oxime synthesis zone per unit of time)/(cyclohexanone fed to the cyclohexanone oxime synthesis zone per unit of time) results in a decrease of the concentration of the organic contaminants in the aqueous reaction medium exiting the hydroxylammonium synthesis zone. Preferably the ratio $f_h/f_c$ is less than 1.00, wherein $f_h$ represents the molar quantity of hydroxylammonium fed to the cyclohexanone oxime synthesis zone per unit of time (in mol per unit of time), and $f_c$ represents the molar quantity of cyclohexanone fed to the cyclohexanone oxime synthesis zone per unit of time (in mol per unit of time).

Preferably, the ratio $f_h/f_c<0.99$, more preferably less than 0.98, in particular lower than 0.97, more in particular lower than 0.96. Decreasing the ratio has the advantage that an effect of the increased concentration hydroxylammonium on the concentration organic contaminants in the aqueous reaction medium exiting the cyclohexanone oxime synthesis zone is mitigated or avoided. These decreased ratios result in a further decrease of the concentration of organic contaminants in the aqueous reaction medium recycled from the cyclohexanone oxime synthesis zone to the hydroxylammonium synthesis zone. There is no specific lower limit for the ratio $f_h/f_c$. Generally $f_h/f_c>0.5$, preferably $f_h/f_c>0.7$, more preferably $f_h/f_c>0.8$. The desired the ratio $f_h/f_c$ may be obtained in various ways. It is for instance possible to decrease the ratio by increasing the flow rate of the cyclohexanone fed to the cyclohexanone oxime synthesis zone relative to the flow rate of the aqueous reaction medium entering the cyclohexanone oxime synthesis zone. It is also possible to decrease the ratio by decreasing the concentration hydroxylammonium in the aqueous reaction medium entering the cyclohexanone oxime synthesis zone.

Generally, the aqueous reaction medium is an acidic, buffered reaction medium. The aqueous reaction medium may contain ammonium ($NH_4^+$), for instance formed as a by-product in the synthesis of hydroxylammonium. Preferably, in the aqueous reaction medium entering the cyclohexanone oxime synthesis zone, the ratio c($NH_4^+$)/c (phosphate) is between 0.1 and 3, more preferably between 0.2 and 2, most preferably between 0.5 and 1.5, wherein c($NH_4^+$) represents the concentration of $NH_4^+$ in mol/l and c(phosphate) represents the phosphate concentration in mol/l.

Generally, the aqueous reaction medium entering the cyclohexanone oxime synthesis zone contains nitrate ($NO_3^-$). Preferably, in the aqueous reaction medium entering the cyclohexanone oxime synthesis zone, the c($NO_3^-$)/c (phosphate) is between 0.05 and 1, more preferably between 0.1 and 0.5, wherein c($NO_3^-$) represents the concentration of $NO_3^-$ in mol/l and c(phosphate) represents the phosphate concentration in mol/l.

In the hydroxylammonium synthesis zone hydroxylammonium is formed by catalytic reduction of nitrate with hydrogen. The hydroxylammonium synthesis zone may be operated at a temperature ranging from 20 to 100° C., preferably 30–90° C., more preferably 40–65° C., and at atmospheric, sub-atmospheric or elevated pressures, preferably between 0.1 and 5 MPa, more preferably between 0.3 and 3 MPa, and in particular between 0.5 and 2 MPa (hydrogen partial pressure). Preferably, the pH in the hydroxylammonium synthesis zone is between 0.5 and 6, more preferably between 1 and 4. The catalyst employed in this zone is generally present in a range of between 1 to 25 wt. %, preferably between 5 to 15 wt. % of a precious metal, relative to total weight of support plus catalyst. Preferably, the catalyst is a palladium containing catalyst, for instance a palladium or a palladium-platinum catalyst, present on a support, such as for instance carbon or alumina support. Generally, the catalyst is present in the hydroxylammonium synthesis zone in an amount of 0.2–5 wt. % relative to the total liquid weight in the hydroxylammonium reactor vessel(s).

DESCRIPTION OF AN EMBODIMENT

Figure 1:
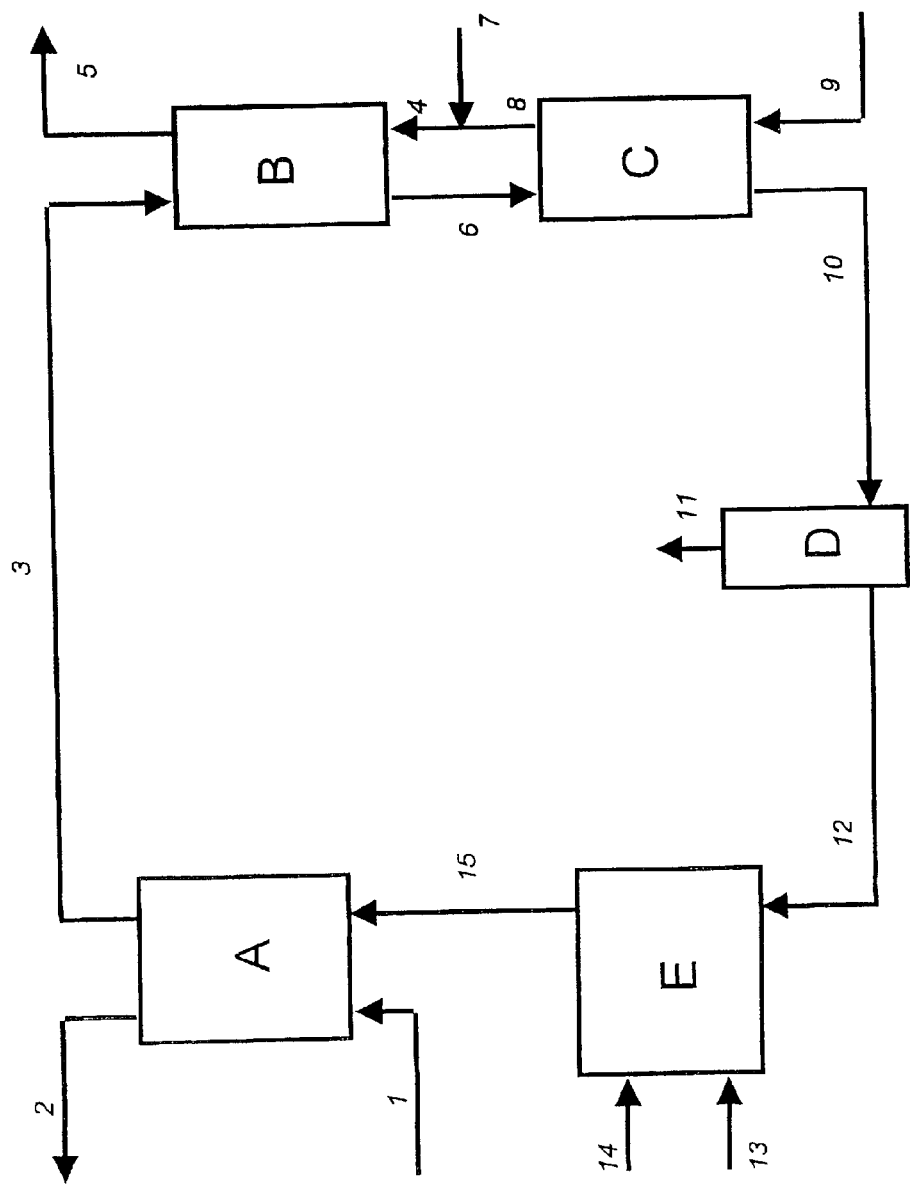
FIG. 1 is a schematic diagram of an embodiment of the process according to the present invention.

Referring to FIG. 1, A represents the hydroxylammonium synthesis zone. A cyclohexanone oxime synthesis zone is used comprising reaction zone B and extraction zone C. To zone A, containing catalyst, hydrogen is fed via line 1; unreacted hydrogen is discharged, with any other gases, via line 2. The aqueous reaction medium, containing, inter alia, phosphate, is fed to zone A through line 15 and after having been enriched in hydroxylammonium (also ammonium as a by-product) in the hydroxylammonium synthesis zone, is passed to the reaction zone B via line 3. The concentration hydroxylammonium in the aqueous reaction medium which is passed from zone A to zone B is higher than 1.0 mol/l. The cyclohexanone to be converted is fed in an organic solvent to the reaction zone B via line 4. The cyclohexanone is introduced into the organic solvent via line 7. The largest part of cyclohexanone oxime produced and dissolved in the organic solvent is removed from the system via line 5.

Upon exiting reaction zone B, the aqueous reaction medium is passed to extraction zone C via line 6. Upon exiting reaction zone B, the hydroxylammonium content of the aqueous reaction medium has been reduced by reaction and contains small quantities of cyclohexanone and cyclohexanone oxime contaminants. The organic solvent enters extraction zone C through line 9. Within extraction zone C, additional cyclohexanone oxime is removed from the aqueous reaction medium and carried out of zone C in the organic solvent through line 8. In the extraction zone C, the residual organic contaminants (cyclohexanone+cyclohexanone oxime) in the aqeuous reaction medium is reduced.

The aqueous reaction medium exits extraction zone C through line 10 which passes the aqueous reaction medium to a separation operation, stripping column D. In this column, cyclohexanone oxime is hydrolyzed to cyclohexanone and the cyclohexanone thus formed together with the cyclohexanone already present is discharged with other organic materials and water (e.g., as an azeotrope) through line 11. The aqueous reaction medium being recycled in the system then passes through line 12 to zone E. In zone E, nitric acid is produced. Preferably, nitric acid is produced, at zone E or thereafter, by reacting air fed through line 13 with ammonia fed through line 14 and with water from the aqueous reaction medium. Directly supplying nitric acid to the aqueous reaction medium instead of producing nitric acid is also possible. Accordingly, the nitrate level is increased in the inorganic medium in zone E. In zone E, ammonium ions, e.g. formed as a by-product in the synthesis of hydroxylammonium, may be converted by means of gases containing nitrogen oxides. However, other methods for removal of ammonium ions may also be used. The aqueous reaction medium then completes the cycle by returning to hydroxylammonium synthesis zone A via line 15. The process is carried out continuously.

The following specific examples are to be construed as merely illustrative, and not limitive, of the remainder of the disclosure.

EXAMPLES 1–7

In all examples the embodiment as illustrated in FIG. 1 was used.

Example 1

In hydroxylammonium synthesis zone A (containing a catalyst (8 wt. % Pd and 2 wt. % Pt supported on carbon), operated at a temperature of 50° C. at a pressure of 1 MPa (hydrogen partial pressure)) an aqueous reaction medium having the following composition 1.00 mol $NH_3OH \cdot H_2PO_4$
1.14 mol $NH_4H_2PO_4$
0.74 mol $H_3PO_4$
1.78 mol $NH_4NO_3$
43.0 mol $H_2O$ was produced per unit of time, and continuously fed (via line 3) to reaction zone B (a pulsed packed column, operated at 55° C.), together with cyclohexanone (supplied via line 7) and toluene (supplied via line 9). The molar ratio $f_h/f_c$ was 0.95. An organic medium comprising cyclohexanone oxime dissolved in toluene was withdrawn from the hydroxylammonium syntheses zone (via line 5), the cyclohexanone oxime concentration being 38 wt. % (relative to the sum weight of toluene+cyclohexanone oxime). The aqueous reaction medium exiting zone B was fed to extraction zone C (a pulsed packed column, operated at 70° C.), together with toluene.

The aqueous reaction medium exiting extraction zone C contained 0.0475 mol/l of hydroxylammonium. Following in-situ formation of nitric acid by absorption of nitrous gases in nitric acid plant E, no hydroxylammonium was found in the aqueous reaction medium entering zone A. The molar quantity of hydroxylammonium lost by decomposition per quantity of hydroxylammonium formed in the hydroxylammonium synthesis zone was 4.75%.

Example 2

In this example all conditions are the same as in example 1 (including the molar ration molar ratio $f_h/f_c$ and the cyclohexanone oxime concentration in the organic medium, except that the aqueous reaction medium exiting zone A and entering zone B had the following composition:

1.25 mol $NH_3OH \cdot H_2PO_4$
1.25 mol $NH_4H_2PO_4$
0.75 mol $H_3PO_4$
1.75 mol $NH_4NO_3$
40.5 mol $H_2O$ The aqueous reaction medium exiting extraction zone C contained 0.0438 mol/l of hydroxylammonium. Following in-situ formation of nitric acid by absorption of nitrous gases in nitric acid plant E, no hydroxylammonium was found in the aqueous reaction medium entering zone A. The molar quantity of hydroxylammonium lost by decomposition per quantity of hydroxylammonium formed in the hydroxylammonium synthesis zone was 3.50%.

Example 3

In this example all conditions are the same as in the previous examples, except that the aqueous reaction medium exiting zone A and entering zone B had the following composition:

1.33 mol $NH_3OH \cdot H_2PO_4$
1.18 mol $NH_4H_2PO_4$ 0.71 mol $H_3PO_4$
1.70 mol $NH_4NO_3$
40.9 mol $H_2O$ The aqueous reaction medium exiting extraction zone C contained 0.0438 mol/l of hydroxylammonium. Following in-situ formation of nitric acid by absorption of nitrous gases in nitric acid plant E, no hydroxylammonium was found in the aqueous reaction medium entering zone A. The molar quantity of hydroxylammonium lost by decomposition per quantity of hydroxylammonium formed in the hydroxylammonium synthesis zone was 3.30%.

Example 4

In this example all conditions are the same as in the previous examples, except that the aqueous reaction medium exiting zone A and entering zone B had the following composition:

1.44 mol $NH_3OH.H_2PO_4$
1.18 mol $NH_4H_2PO_4$
0.71 mol $H_3PO_4$
1.86 mol $NH_4NO_3$
39.3 mol $H_2O$ The aqueous reaction medium exiting extraction zone C contained 0.0463 mol/l of hydroxylammonium. Following in-situ formation of nitric acid by absorption of nitrous gases in nitric acid plant E, no hydroxylammonium was found in the aqueous reaction medium entering hydroxylammonium synthesis zone A. The molar quantity of hydroxylammonium lost by decomposition per quantity of hydroxylammonium formed in the hydroxylammonium synthesis zone was 3.22%.

Example 5

In this example all conditions are the same as in the previous examples, except that the aqueous reaction medium exiting zone A and entering zone B had the following composition:

1.48 mol $NH_3OH.H_2PO_4$
1.64 mol $NH_4H_2PO_4$
0.69 mol $H_3PO_4$
1.41 mol $NH_4NO_3$
38.3 mol $H_2O$ The aqueous reaction medium exiting extraction zone C contained 0.0375 mol/l of hydroxylammonium. Following in-situ formation of nitric acid by absorption of nitrous gases in nitric acid plant E, no hydroxylammonium was found in the aqueous reaction medium entering zone A. The molar quantity of hydroxylammonium lost by decomposition per quantity of hydroxylammonium formed in the hydroxylammonium synthesis zone was 2.54%.

Example 6

In this example all conditions are the same as in the previous examples, except that the aqueous reaction medium exiting zone A and entering zone B had the following composition:

1.54 mol $NH_3OH.H_2PO_4$
1.63 mol $NH_4H_2PO_4$
0.71 mol $H_3PO_4$
1.53 mol $NH_4NO_3$
37.2 mol $H_2O$ The aqueous reaction medium exiting extraction zone C contained 0.0188 mol/l of hydroxylammonium. Following in-situ formation of nitric acid by absorption of nitrous gases in nitric acid plant E, no hydroxylammonium was found in the aqueous reaction medium entering zone A. The molar quantity of hydroxylammonium lost by decomposition per quantity of hydroxylammonium formed in the hydroxylammonium synthesis zone was 1.22%.

Example 7

In this example all conditions are the same as in the previous examples, except that the aqueous reaction medium exiting zone A and entering zone B had the following composition:

1.63 mol $NH_3OH.H_2PO_4$
1.65 mol $NH_4H_2PO_4$
0.70 mol $H_3PO_4$
1.51 mol $NH_4NO_3$
36.5 mol $H_2O$ The aqueous reaction medium exiting extraction zone C contained 0.0163 mol/l of hydroxylammonium. Following in-situ formation of nitric acid by absorption of nitrous gases in nitric acid plant E, no hydroxylammonium was found in the aqueous reaction medium entering hydroxylammonium synthesis zone A. The molar quantity of hydroxylammonium lost by decomposition per quantity of hydroxylammonium formed in the hydroxylammonium synthesis zone was 1.00%.

The results of examples 1 to 7 have been summarized in table 1, showing the molar quantity of hydroxylammonium lost by decomposition per quantity of hydroxylammonium formed in the hydroxylammonium synthesis zone (in %) and the conversion of hydroxylammonium. It is shown that an increase of the concentration hydroxylammonium in the aqueous reaction medium entering the cyclohexanone oxime synthesis zone results in a decrease of the molar quantity of hydroxylammonium lost by decomposition per quantity of hydroxylammonium formed in the hydroxylammonium synthesis zone, and in an increase of the conversion of hydroxylammonium.

| Ex. | $c(NH_3OH^+)_{in}$ (mol/l) | $c(NH_3OH^+)_{out}$ (mol/l) | Conversion of $NH_3OH^+$ (%) | loss of $NH_3OH^+$ (%) |
|---|---|---|---|---|
| 1 | 1.00 | 0.0475 | 95.25 | 4.75 |
| 2 | 1.25 | 0.0438 | 96.5 | 3.50 |
| 3 | 1.33 | 0.0438 | 96.7 | 3.30 |
| 4 | 1.44 | 0.0463 | 96.78 | 3.22 |
| 5 | 1.48 | 0.0375 | 97.46 | 2.54 |
| 7 | 1.54 | 0.0188 | 98.78 | 1.22 |
| 9 | 1.63 | 0.0163 | 99.0 | 1.00 |

Particular embodiments of this invention have been illustrated and described above. However, those of ordinary skill in the art understand that various modifications can be made, without departing from the spirit and scope of the invention. Accordingly, interpretation of this invention should not be limited, except as by the appended claims.

What is claimed is:

1. Process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone in the presence of an organic solvent to form cyclohexanone oxime, characterized in that the concentration hydroxylammonium in the aqueous reaction medium entering the cyclohexanone oxime synthesis zone is higher than 1.0 mol/l.

2. Process according to claim 1, wherein the concentration hydroxylammonium in the aqueous reaction medium entering the cyclohexanone oxime synthesis zone is higher than 1.2 mol/l.

3. Process according to claim 1, wherein the concentration hydroxylammonium in the aqueous reaction medium entering the cyclohexanone oxime synthesis zone is higher than 1.4 mol/l.

4. Process according to claim 1, wherein the concentration hydroxylammonium in the aqueous reaction medium entering the cyclohexanone oxime synthesis zone is higher than 1.6 mol/l.

5. Process according to claim 1, wherein the aqueous reaction medium and a stream comprising the cyclohexanone and the organic solvent are contacted in countercurrent flow.

6. Process according to claim 1, wherein the organic solvent and cyclohexanone are fed to the cyclohexanone oxime synthesis zone, and an organic medium comprising the organic solvent and the cyclohexanone oxime are withdrawn from the cyclohexanone oxime synthesis zone, the cyclohexanone oxime concentration in the organic medium being higher than 5 wt. %.

7. Process according to claim 6, wherein the cyclohexanone oxime concentration in the organic medium exiting the cyclohexanone oxime synthesis zone is higher than 25 wt. %.

8. Process according to claim 1, wherein the organic solvent is selected from the group consisting of benzene, toluene, xylene, cyclohexane, and mixtures thereof.

9. Process according to claim 1, wherein the concentration hydroxylammonium in the aqueous reaction medium exiting the cyclohexanone oxime synthesis zone is less than 0.1 mol/l.

10. Process according to claim 9, wherein the concentration hydroxylammonium in the aqueous reaction medium exiting the cyclohexanone oxime synthesis zone is between 0.01 and 0.05 mol/l.

* * * * *